United States Patent
Zhang et al.

(10) Patent No.: US 11,364,349 B2
(45) Date of Patent: Jun. 21, 2022

(54) INJECTION END AND SAFETY SYRINGE THEREOF

(71) Applicant: Zhejiang Kindly Medical Devices Co., Ltd., Zhejiang (CN)

(72) Inventors: Qian Zhang, Zhejiang (CN); Hong Chen, Zhejiang (CN); Zhuoyuan Lou, Zhejiang (CN)

(73) Assignee: ZHEJIANG KINDLY MEDICAL DEVICES CO., LTD., Wenzhou (CN)

( * ) Notice: Subject to any disclaimer, the term of this patent is extended or adjusted under 35 U.S.C. 154(b) by 333 days.

(21) Appl. No.: 16/550,286

(22) Filed: Aug. 26, 2019

(65) Prior Publication Data

US 2020/0069886 A1 Mar. 5, 2020

(30) Foreign Application Priority Data

Aug. 31, 2018 (CN) .......................... 201811010144.X

(51) Int. Cl.
*A61M 5/32* (2006.01)
*A61M 5/31* (2006.01)

(52) U.S. Cl.
CPC ........ *A61M 5/3232* (2013.01); *A61M 5/3204* (2013.01); *A61M 2005/3126* (2013.01); *A61M 2005/3208* (2013.01); *A61M 2205/0233* (2013.01); *A61M 2205/0294* (2013.01); *A61M 2205/50* (2013.01)

(58) Field of Classification Search
CPC .... A61M 2005/206; A61M 2005/3126; A61M 5/20; A61M 5/31; A61M 5/3204; A61M 5/3232; A61M 2005/3208; A61M 2205/0233; A61M 2205/0294; A61M 2205/50; A61M 5/326; A61M 2005/3247; A61M 2005/3267; A61M 5/3272; A61M 5/3271
See application file for complete search history.

(56) References Cited

U.S. PATENT DOCUMENTS

| 8,858,510 | B2* | 10/2014 | Karlsson | A61M 5/3272 604/198 |
| 2007/0112310 | A1* | 5/2007 | Lavi | A61M 5/2033 604/245 |
| 2016/0089501 | A1* | 3/2016 | Soerensen | A61M 5/31583 604/506 |
| 2020/0038593 | A1* | 2/2020 | Keller | A61M 15/00 |

* cited by examiner

*Primary Examiner* — Rebecca E Eisenberg

(57) ABSTRACT

A needle end and a safety syringe are provided, belonging to technical field of medical instruments. The safety syringe includes an injection end, a liquid storage device, and a base. The injection end includes a needle base, an injection needle, and a needle guard assembly. The injection needle is fixed to the needle base. The needle guard assembly is connected to the needle base. The needle guard assembly includes a protective casing and a spring, wherein a first terminal of the spring is connected to the needle base and a second terminal of the spring is connected to the protective casing. The liquid storage device includes a liquid storage container and a liquid storage sleeve. The liquid storage is sleeved on an outer surface the liquid storage container, wherein the liquid storage container is detachably connected to the injection end. The base is detachably connected to the liquid storage device.

18 Claims, 16 Drawing Sheets

INJECTION END AND SAFETY SYRINGE THEREOF

BACKGROUND OF THE INVENTION

Field of the Disclosure

The present invention relates to the technical field of medical instruments, and more particularly to an injection end and a safety syringe thereof.

Description of Related Art

The incidence of diabetes is increasing, and it has become the third biggest killer followed by cardiovascular and cerebrovascular diseases and cancer. It is currently believed that insulin injection therapy is an effective method for treating diabetes. Intensive treatment with insulin injection can make patients' blood sugar, blood lipids, blood pressure and BMI meet the standard.

At present, an insulin pump and an insulin pen are mostly used for insulin injection. In an invention patent of the application No. CN201310055639.5, an insulin injection pen is disclosed. The insulin injection pen can be repeatedly used through repeated adjustment of the positioning block, the rotary spring, and the clutch spring, thereby realizing multiple times of uses. However, this manual injection method is inaccurate for injection dose control. An utility model patent of the application No. CN201320592093.2 relates to an insulin refill injection pen capable of automatically completing an injection action. In particular, an automatic control power device is provided, which adopts a single-chip microcomputer and a micro-motor. After the injection dose is set, it can automatically push the needle, automatically push medicine, and automatically pull the needle after 6 seconds of automatic subcutaneous stay, which can eliminate the patient's fear of injection. But it needs to use the battery to provide electric energy, which brings inconvenience for replacing the battery. Furthermore, the needle tip used with the insulin pen is very small, and the cap wall of the needle cap is too thin, so the needle can easily puncture the side wall of the needle cap during operation. It is easy to cause patients or hospital care staffs to be stabbed by the needle tip during operation, and there is a great risk of infection.

In view of this, the inventors of the present invention have finally created the injection end and the safety syringe of the present invention after a long period of research and practice.

It should be noted that the above description of the technical background is merely for the purpose of facilitating a clear and complete description of technical solutions of the present invention, and is convenient for understanding by those skilled in the art. The above technical solutions should not be considered to be well-known to those skilled in the art, simply because these aspects are set forth in background section of the present invention.

SUMMARY OF THE INVENTION

In order to solve the above problems, it is an object of the present invention to provide an injection end and a safety syringe thereof.

According to an exemplary embodiment, an injection end for a safety syringe is provided. The injection end includes a needle base, an injection needle, and a needle guard assembly. The injection needle is fixed to the needle base. The needle guard assembly is connected to the needle base. The needle guard assembly includes a protective casing and a spring, wherein a first terminal of the spring is connected to the needle base and a second terminal of the spring is connected to the protective casing.

In one embodiment, when the injection end is in a pre-use status, the protective casing is rotated to the left or to the right to cause a torsion force to the spring, the injection needle is hidden inside the protective casing, and the protective casing is subjected to the torsion force along a torsion direction of the spring.

In one embodiment, when the injection end is in an in-use status, the injection needle is pressed against skin, the injection needle is automatically exposed out from the protective casing and punctured, the spring is in a compressed state, and the protective casing is rotated out from a first locking groove on the protective casing by the torsion force of the spring.

In one embodiment, when the injection end is in a post-use status, the injection needle is pulled out from the skin, the protective casing is moved away from the skin due to an elastic force of the compressed spring, the protective casing is automatically rotated due to the torsion force of the spring, and the injection needle is hidden inside the protective casing again.

In one embodiment, the protective casing is further provided with a locking structure and a first limiting groove, and the locking structure further comprises a first locking groove and a second locking groove; and an outer face of the needle base is disposed with a convex structure matched with the first limiting groove, the first locking groove, and the second locking groove.

In one embodiment, the injection end further includes a protective sleeve, and the protective sleeve is fixedly connected with the needle base to protect the protective casing therein, so that the protective casing is untouched when the injection end is in an in-use status, and the convex structure of the needle base is prevented from coining off the protective casing.

In one embodiment, a bottom portion of the needle base is provided with a screw thread buckle, so that the injection end is detachably connected to a liquid storage device.

According to another exemplary embodiment, a safety syringe is provided. The safety syringe includes an injection end, a liquid storage device, and a base. The injection end includes a needle base, an injection needle, and a needle guard assembly. The injection needle is fixed to the needle base. The needle guard assembly is connected to the needle base. The needle guard assembly includes a protective casing and a spring, wherein a first terminal of the spring is connected to the needle base and a second terminal of the spring is connected to the protective casing. The liquid storage device includes a liquid storage container and a liquid storage sleeve. The liquid storage is sleeved on an outer surface the liquid storage container, wherein the liquid storage container is detachably connected to the injection end. The base is detachably connected to the liquid storage device.

In one embodiment, when the injection end is in a pre-use status, the protective casing is rotated to the left or to the right to cause a torsion force to the spring, the injection needle is hidden inside the protective casing, and the protective casing is subjected to the torsion force along a torsion direction of the spring.

In one embodiment, when the injection end is in an in-use status, the injection needle is pressed against skin, the injection needle is automatically exposed out from the protective casing and punctured, the spring is in a compressed state, and the protective casing is rotated out from a first locking groove on the protective casing by the torsion force of the spring.

In one embodiment, when the injection end is in a post-use status, the injection needle is pulled out from the skin, the protective casing is moved away from the skin due to an elastic force of the compressed spring, the protective casing is automatically rotated due to the torsion force of the spring, and the injection needle is hidden inside the protective casing again.

In one embodiment, the protective casing is further provided with a locking structure and a first limiting groove, and the locking structure further comprises a first locking groove and a second locking groove; and an outer face of the needle base is disposed with a convex structure matched with the first limiting groove, the first locking groove, and the second locking groove.

In one embodiment, the injection end further comprises a protective sleeve, and the protective sleeve is fixedly connected with the needle base to protect the protective casing therein, so that the protective casing is untouched when the injection end is in an in-use status, and the convex structure of the needle base is prevented from coining off the protective casing.

In one embodiment, a bottom portion of the needle base is provided with a screw thread buckle, so that the injection end is detachably connected to the liquid storage device.

In one embodiment, the liquid storage device further includes a screw thread and a piston. The screw thread is matched to the screw thread buckle, disposed on an upper portion of the liquid storage container, and configured to achieve a detachable connection between the injection end and the liquid storage device. The piston is disposed in a bottom portion of the liquid storage container, wherein the piston is slidablely moving inside the liquid storage container by an external force.

In one embodiment, the liquid storage sleeve further includes a visible window, a scale line, and a clamping protrusion. The visible window and the scale line are disposed on an outer surface of the liquid storage sleeve, allowing a user to observe a solvent dose inside the liquid storage container. The clamping protrusion is disposed at a bottom portion of the liquid storage sleeve, and is configured to detachably connect with the base.

In one embodiment, the safety syringe further includes a driving device, a microprocessor, an energy storage component, and an energy converter. The driving device is configured to drive the liquid storage container for injection. The driving device includes a power unit and a transmission unit electrically connected to the power unit. The microprocessor is configured to control the driving device. The energy storage component is configured to provide energy to the microprocessor and the driving device. The energy converter is configured to convert mechanical energy into electrical energy, and transmit the electrical energy to the energy storage component. The power unit, the energy storage component, the energy converter, and the microprocessor constitute an electronically-controlled component, mounted in an electronically-controlled component housing. The electronically-controlled component housing is fixedly connected to the base.

In one embodiment, the energy converter further includes a substrate layer, a second seed layer, a second conductive layer, a piezoelectric layer, and a fourth conductive layer. A first opening and a second opening are respectively disposed on a front surface and a back surface of the substrate layer. The second seed layer is located at the first opening. The second conductive layer is located on the second seed layer. The piezoelectric layer is located on the second conductive layer, wherein a first surface of the piezoelectric layer is flush with the first opening. The fourth conductive layer is located on the piezoelectric layer. The second opening includes a raised end, and the raised end is a mass block. The substrate layer, the second feed layer, the second conductive layer, the piezoelectric layer, and the fourth conductive layer constitutes a cantilever beam, except the mass block.

In one embodiment, the energy converter includes a substrate layer, a second conductive adhesive layer, a third conductive layer, and a piezoelectric layer. A first opening and a second opening are respectively disposed on a front surface and a back surface of the substrate layer. The second conductive adhesive layer is located at the first opening. The third conductive layer is located on the second conductive adhesive layer. The piezoelectric layer is located on the third conductive layer, wherein a first surface of the piezoelectric layer is flush with the first opening. The second opening includes a raised end, and the raised end is a mass block. The substrate layer, the second conductive adhesive layer, the third conductive layer, and the piezoelectric layer constitutes a cantilever beam, except the mass block.

In one embodiment, an interdigital electrode is formed by the third conductive layer, and the interdigital electrode further includes a first electrode layer and a second electrode layer, and the first electrode layer and the second electrode layer have opposite polarities.

Compared with the prior art, the present invention has the following advantages. An injection end and a safety syringe are provided in the present invention. The safety syringe includes an injection end, a liquid storage device, and a base. Furthermore, a driving device, a power unit, a transmission unit, a microprocessor, an energy storage component, and an energy converter are mounted in an electronically-controlled component housing, wherein the electronically-controlled component housing is fixedly connected to the base. The accuracy of the liquid inhalation amount is ensured while achieving automatic injection, wherein the energy converter converts mechanical energy into electrical energy, while storing electrical energy through the energy storage component, for providing electrical energy to the power unit and the microprocessor. A portion of energy is recycled for avoiding energy waste, which can save manpower, material resources and money, and reduce energy consumption. The needle guard assembly is disposed at the injection end, which can effectively prevent patients or hospital care staffs from being stabbed by the needle tip during operation, and can keep away from the infection risk.

BRIEF DESCRIPTION OF THE DRAWINGS

Aspects of the present invention are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DESCRIPTION OF THE INVENTION

Figure 1A:
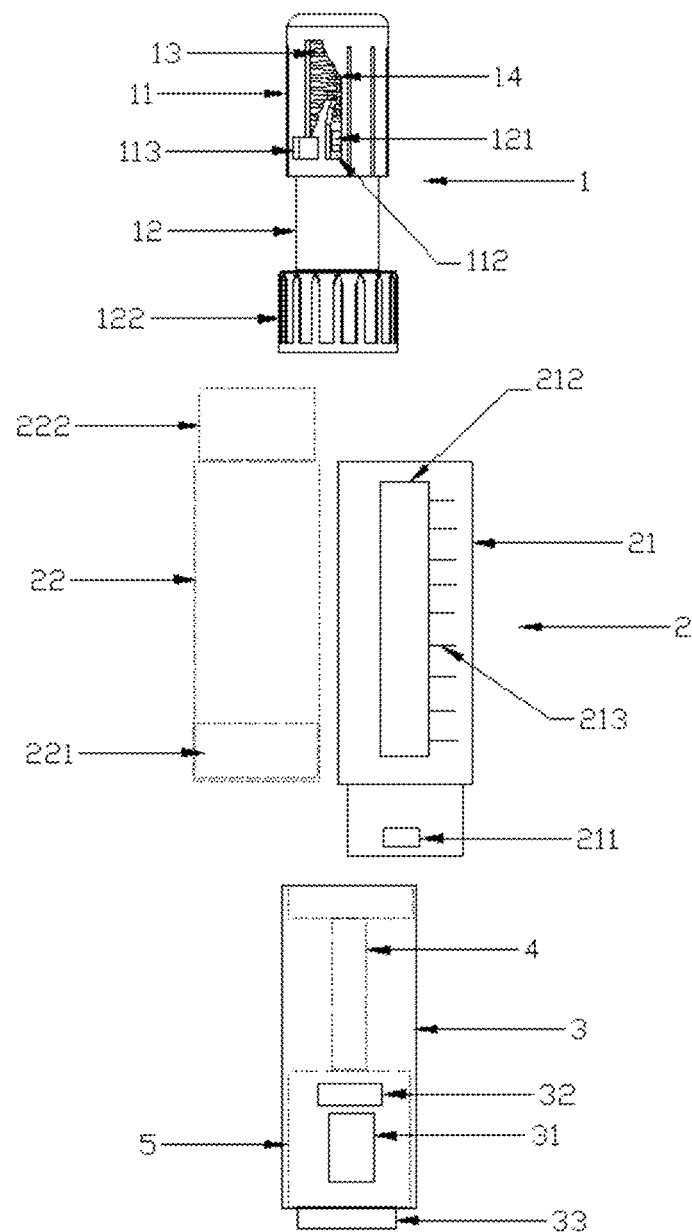
FIG. 1A is a structural diagram of a safety syringe according to an embodiment of the present invention.

The following disclosure provides many different embodiments, or examples, for implementing different features of the provided subject matter. Specific examples of components and arrangements are described below to simplify the present invention. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present invention may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

Embodiment 1

Figure 1B:
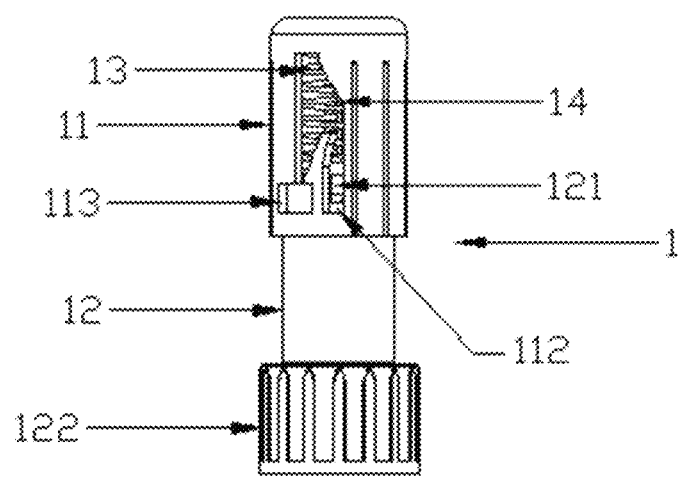
FIG. 1B is a structural diagram of an injection end of the safety syringe in Embodiment 1 of the present invention.
Figure 1C:
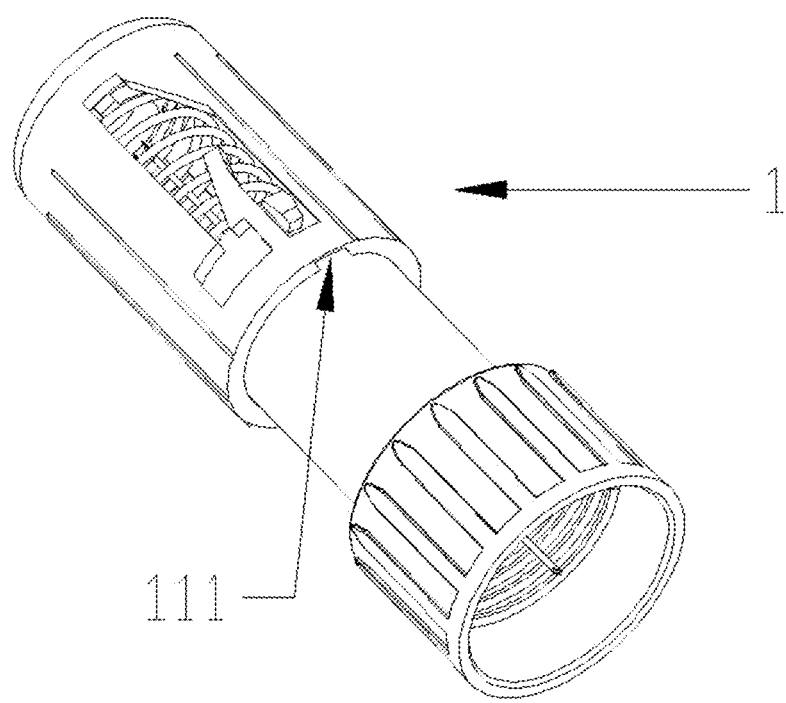
FIG. 1C is a three-dimensional structural diagram of an injection end of the safety syringe in Embodiment 1 of the present invention.

Please refer to FIG. 1A, FIG. 1B, and FIG. 1C.

FIG. 1A is a structural diagram of a safety syringe according to an embodiment of the present invention.

FIG. 1B is a structural diagram of an injection end of the safety syringe in Embodiment 1 of the present invention.

FIG. 1C is a three-dimensional structural diagram of an injection end of the safety syringe in Embodiment 1 of the present invention.

A safety syringe and an injection end 1 are provided in Embodiment 1. The safety syringe includes an injection end 1, a liquid storage device 2, and a base 3. The injection end 1 includes a needle base 12, an injection needle 14, and a needle guard assembly. The injection needle 14 is fixed to the needle base 12. The needle guard assembly is connected to the needle base 12. The needle guard assembly includes a protective casing 11 and a spring 13, wherein a first terminal of the spring 13 is connected to the needle base 12 and a second terminal of the spring 13 is connected to the protective casing 11.

The liquid storage device 2 includes a liquid storage container 22 and a liquid storage sleeve 21. The liquid storage sleeve 21 is sleeved on an outer surface of the liquid storage container 22, wherein the liquid storage container 22 is detachably connected to the injection end 1.

The base 3 is detachably connected to the liquid storage device 2.

In a specific implementation of the present invention, the protective casing 11 is further provided with a locking structure and a first limiting groove 111 (see FIG. 1C), and the locking structure further includes a first locking groove 112 and a second locking groove 113. An outer surface of the needle base 12 is disposed with a convex structure 121 matched with the first limiting groove 111, the first locking groove 112, and the second locking groove 113.

In a specific implementation of the present invention, a bottom portion of the needle base 12 is provided with a screw thread buckle 122, so that the injection end 1 is detachably connected to the liquid storage device 2. Therefore, it is easy to replace the injection end 1, which is easy and safe to use.

In a specific implementation of the present invention, the liquid storage sleeve 21 further includes a visible window 212 and a scale line 213 disposed on an outer surface of the liquid storage sleeve 21, allowing a user to observe a solvent dose inside the liquid storage container 22. A clamping protrusion 211 is disposed at a bottom portion of the liquid storage sleeve 21, and is configured to detachably connect with the base 3.

In another specific implementation of the present invention, the liquid storage container 22 further includes a screw thread 222 matched to the screw thread buckle 122, wherein the screw thread 222 is configured to achieve a detachable connection between the injection end 1 and the liquid storage device 2. A piston 221 is disposed in a bottom portion of the liquid storage container 22, wherein the piston 221 is slidably moving inside the liquid storage container 22 by an external force.

Figure 2:
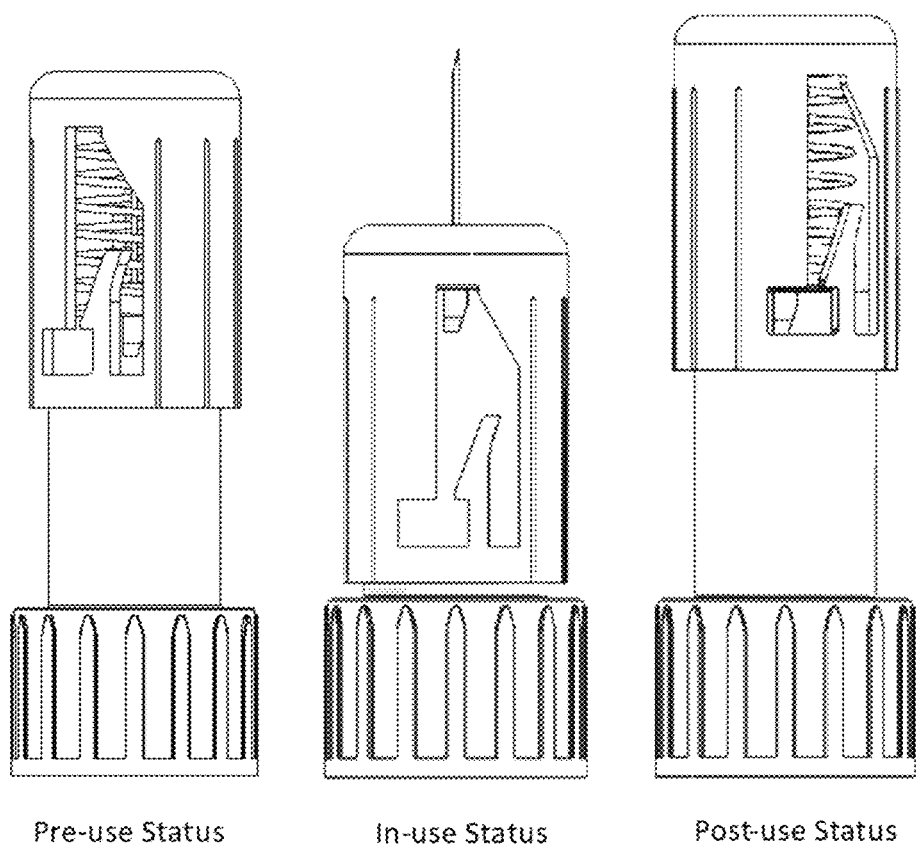
FIG. 2 is a schematic diagram showing different use statuses of an injection end of the safety syringe according to an embodiment of the present invention.

Please refer to FIG. 2.

FIG. 2 is a schematic diagram showing different use statuses of an injection end of the safety syringe according to an embodiment of the present invention.

When the injection end 1 is in a pre-use status, the protective casing 11 needs to be rotated to the left or to the right to cause a torsion force to the spring 13, so that the convex structure 121 of the needle base 2 enters along the first limiting groove 111, and finally stops at the second limiting groove 112. At this time, the injection needle 14 is hidden inside the protective casing 11, and the protective casing 11 is subjected to a torsion force along a torsion direction of the spring 13.

When the injection end 1 is in an in-use status, the injection needle 14 is pressed against skin, and the injection needle 14 is automatically exposed out from the protective casing 11 and punctured. At this time, the spring 13 is in a compressed state, and the protective casing 11 is rotated out from a first locking groove 112 on the protective casing 11 by the torsion force of the spring 13.

When the injection end 1 is in a post-use status, the injection needle 14 is pulled out from the skin, the protective casing 11 is moved away from the skin due to an elastic force of the compressed spring 13. At this time, the protective casing 11 is automatically rotated due to the torsion force of the spring 13, the convex structure 121 of the needle base 12 finally stops at the second locking groove 113, and the injection needle 14 is hidden inside the protective casing 11 again. Therefore, the protective casing 11 can effectively prevent a patient or a hospital care worker from being stabbed by the needle tip of the injection needle 14 during operation, which can be away from the risk of infection.

Embodiment 2

Figure 3:
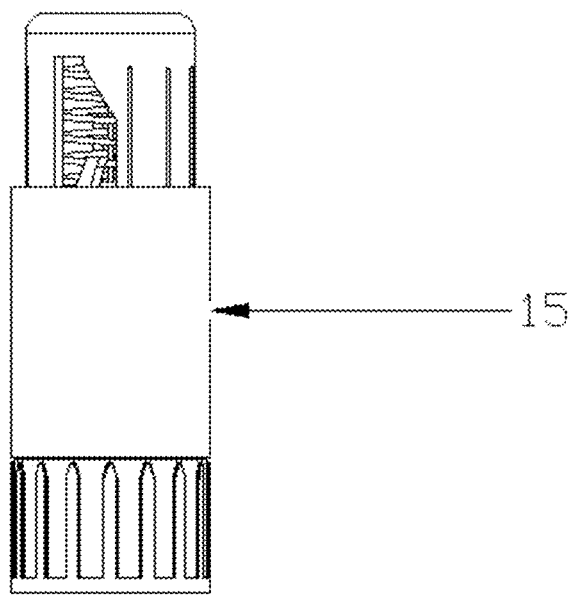
FIG. 3 is a structural diagram of an injection end of the safety syringe in Embodiment 2 of the present invention.

Please refer to FIG. 3.

FIG. 3 is a structural diagram of an injection end of the safety syringe in Embodiment 2 of the present invention.

The injection end shown in Embodiment 2 is similar to the injection end 1 shown in Embodiment 1, and the difference between them is that the injection end 1 in Embodiment 2 further includes a protective sleeve 15. The protective sleeve 15 is fixedly connected with the needle base 12 to protect the protective casing 11 therein, so that the protective casing 11 is untouched when the injection end 1 is in an in-use status, and the convex structure 121 of the needle base 12 is prevented from coining off the protective casing 11, causing the safety structure to fail.

Embodiment 3

Figure 4:
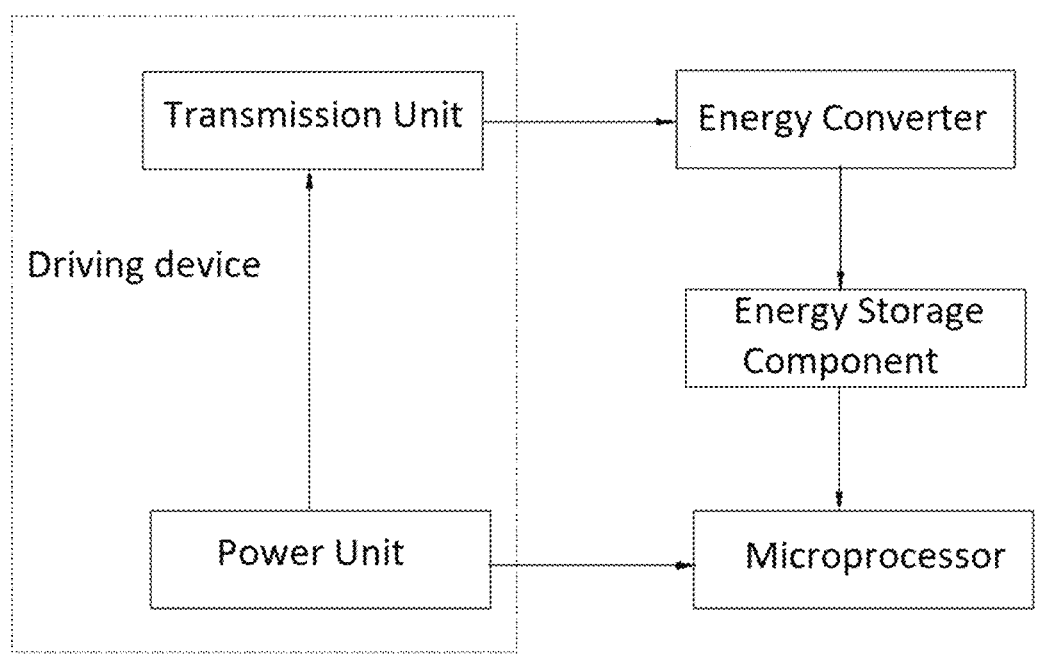
FIG. 4 is a block diagram of components disposed in a base of the safety syringe in Embodiment 3 of the present invention.

Please refer to FIG. 4,

FIG. 4 is a block diagram of components disposed in a base 3 of the safety syringe in Embodiment 3 of the present invention.

As shown in FIG. 4, a driving device, a microprocessor, an energy storage component, and an energy converter are disposed in the base 3 of the safety syringe. The driving device is configured to drive the liquid storage container 22 for injection. The driving device further includes a power unit and a transmission unit 4 electrically connected to the power unit. The microprocessor is configured to control the driving device. The energy storage component is configured to provide energy to the microprocessor and the driving device. The energy converter is configured to convert mechanical energy into electrical energy, and transmit the electrical energy to the energy storage component. The power unit, the energy storage component, the energy converter, and the microprocessor constitute an electronically-controlled component, mounted in an electronically-controlled component housing 5. The electronically-controlled component housing 5 is fixedly connected to the base 3. The power unit is configured to provide power to the liquid storage container 22, and the transmission unit is configured to transmit power to the liquid storage container 22, thereby pushing the piston 221 to move forward for injection. The power unit, the transmission unit, the energy converter, the energy storage component, and the microprocessor are electrically connected in sequence, and the microprocessor is further electrically connected to the power unit. The microprocessor includes a detection module, a data reception processing module, and a control module. The detection module, the data reception processing module, and the control module are sequentially connected.

As shown in FIG. 1A, an operation platform is disposed on the outside of the base 3. The operation platform includes a display screen 31 and a button area 32. The bottom portion of the base 3 is provided with a touch switch 33, wherein the touch switch 33 is connected to the microprocessor. After the user sets the injection dose through the operation platform, the touch switch 33 is activated. At this time, an activation signal is detected by the detection module, data is received and processed by the data reception processing module, the power unit is controlled to be activated by the control module, and the power unit is rotated according to a certain rotation speed and a certain period of time. The transmission unit then pushes the piston 221 of the liquid storage container 22 to move forward to achieve automatic injection. This kind of automatic injection ensures the accuracy of the liquid inhalation amount and avoids adverse effects of mitigation condition due to the difference in the liquid inhalation amount.

At the same time, the energy converter detects mechanical energy generated by the transmission unit during operation, and converts mechanical energy into electrical energy, while storing electrical energy through the energy storage component, for providing electrical energy to the power unit and the microprocessor. A portion of energy is recycled for avoiding energy waste, which can save manpower, material resources and money, and reduce energy consumption.

Embodiment 4

Please refer to FIGS. 5-9.

Figure 5:
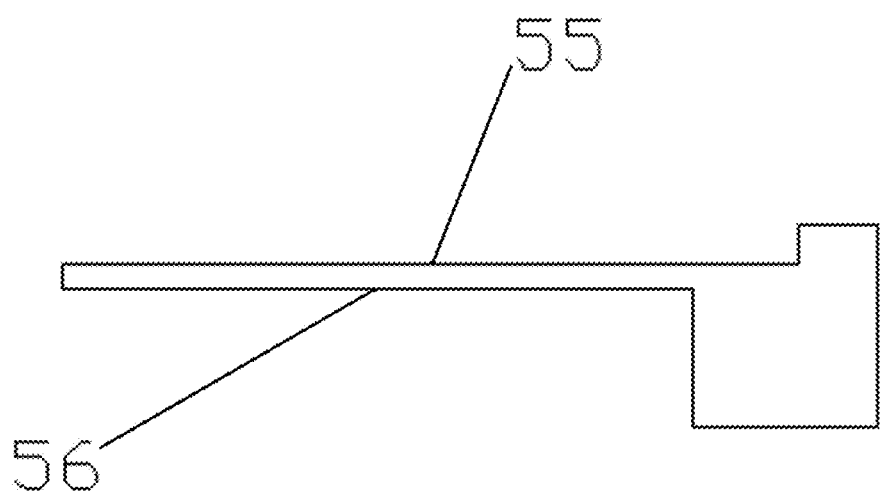
FIG. 5 is a structural diagram of a substrate layer according to an embodiment of the present invention.

FIG. 5 is a structural diagram of a substrate layer according to an embodiment of the present invention.

Figure 6:
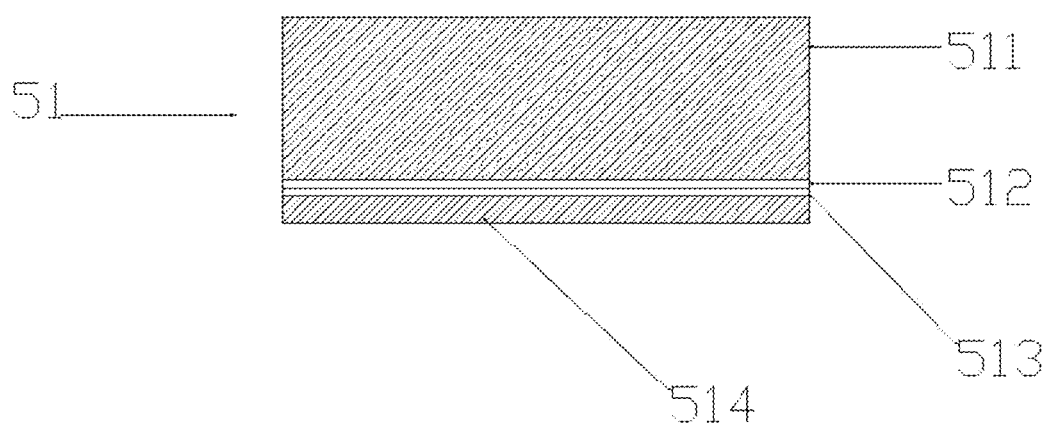
FIG. 6 is a structural diagram of a piezoelectric layer in Embodiment 4 of the present invention.

FIG. 6 is a structural diagram of a piezoelectric layer in Embodiment 4 of the present invention.

Figure 7:
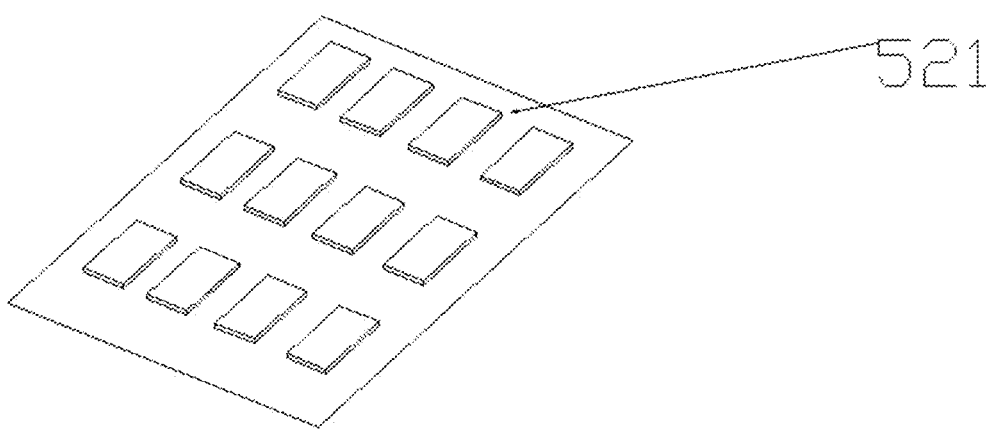
FIG. 7 is a structural diagram showing that a protective layer is disposed on a substrate layer in Embodiment 4 of the present invention.

FIG. 7 is a structural diagram showing that a protective layer is disposed on a substrate layer in Embodiment 4 of the present invention.

Figure 8:
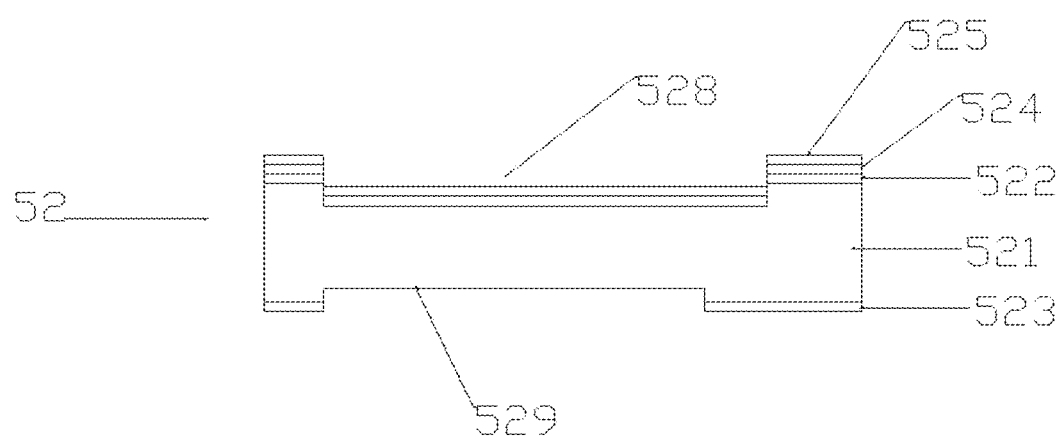
FIG. 8 is a structural diagram of a substrate layer in Embodiment 4 of the present invention.

FIG. 8 is a structural diagram of a substrate layer in Embodiment 4 of the present invention.

Figure 9:
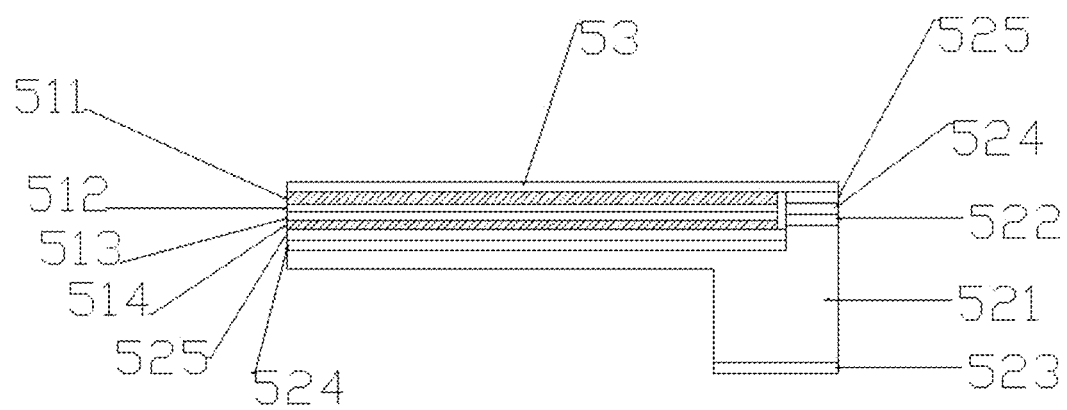
FIG. 9 is a structural diagram of an energy converter in Embodiment 4 of the present invention.

FIG. 9 is a structural diagram of an energy converter in Embodiment 4 of the present invention.

In a specific implementation of the present invention, the energy converter may include a substrate 52. As shown in FIG. 8, the substrate 52 includes a substrate layer 521, a second seed layer 524, a second conductive layer 525, a piezoelectric layer 51, and a fourth conductive layer 53. A first opening 55 and a second opening 56 are respectively disposed on a front surface and a back surface of the substrate layer 521 (see FIG. 5). The substrate layer 521 may be a crystalline silicon wafer layer. The second seed layer 524 is located at the first opening 55. The second conductive layer 525 is located on the second seed layer 524. The piezoelectric layer 51 is located on the second conductive layer 525, wherein a first surface of the piezoelectric layer 51 is flush with the first opening 55. The fourth conductive layer 53 is located on the piezoelectric layer 51. The second opening 56 may include a raised end, and the raised end is a mass block. Be noted that, the substrate layer 521, the second feed layer 524, the second conductive layer 525, the piezoelectric layer 51, and the fourth conductive layer 53 constitutes a cantilever beam, except the mass block. The cantilever beam is used for fixedly connected with the electronically-controlled component housing 5. When the transmission unit is moving, the cantilever beam generates forced vibration under the driving action of environmental vibration, and the mass block located at the free end of the cantilever beam drives the cantilever beam to reciprocate up and down, thereby causing a zirconium titanate material layer on the cantilever beam to be stretched or compressed to produce mechanical strain. Based on the positive piezoelectric effect, free charges are generated on the first conductive layer and the third conductive layer on the upper surface and the lower surface of the zirconium titanate material layer, and then a current is generated, that is, electrical energy is outputted outward.

In practical applications, as shown in FIG. 6, the piezoelectric layer 51 is provided with a piezoelectric material layer 511, a first seed layer 512, a first conductive layer 513, and a first adhesive layer 514 in an order from top to bottom. The piezoelectric material layer 511 may be a lead zirconate titanate material layer.

The specific processing technology of the energy converter is as follows:

Step 1: Preparation of the Piezoelectric Layer 51.

In FIG. 6, on the piezoelectric material layer 511, a Cr layer is sequentially sputtered as a first seed layer 512, an Au layer is evaporated as the first conductive layer 513, and finally an epoxy resin is applied as the first conductive adhesive layer 514. The Cr layer as the first seed layer 512 usually has a thickness of 200 Å to 2000 Å, but should not be lower than 200 Å. The Au layer as the first conductive layer 513 usually has a thickness of 2000 Å~10 nm, but should not be lower than 2000 Å. The first conductive adhesive layer 514 is an epoxy resin doped with silver crumb, which has bonding characteristics and electrical conductivity, and can perform good bonding.

Step 2: Pre-Treatment of the Substrate Layer 521.

As shown in FIG. 8, a first protective layer 522 and a second protective layer 523 are respectively disposed on the front surface and the back surface of the substrate layer 521, a first recess 528 is formed between the first protective layer 522 and the substrate layer 521, and a second recess 529 is formed between the second protective layer 523 and the substrate layer 521, wherein the first protective layer 522 and the second protective layer 523 are $Si_3N_4$. The thickness of the $Si_3N_4$ layer is from 2000 Å to 5000 Å, but should not be less than 2000 Å. After etching the crystal silicon wafer with a 30% potassium hydroxide solution at a temperature of 70° C., the longitudinal height of the first recess 528 and the longitudinal height of the second recess 529 are increased. At this time, a second seed layer 524 and a second conductive layer 525 are sequentially disposed on the first protective layer 522, wherein the second seed layer 524 is a Cr layer, and the second conductive layer 525 is an Au layer. Since the lattice constant of Au is relatively different from the lattice constant of Si, the presence of the second seed layer 524 facilitates the formation of an Au film thereon. The thickness of the Cr layer is generally 200 Å to 2000 Å, but should not be less than 200 Å. The thickness of the Au layer is usually 2000 Å~10 nm, but should not be less than 2000 Å. The substrate layer 521 is pre-treated to form the substrate 52.

Step 3: Bonding.

The piezoelectric layer 51 in Step 1 and the substrate 52 is Step 2 are bonded together under high temperature and high pressure. The lateral width of the piezoelectric layer 51 is smaller than the lateral width of the first recess 528. The bonding condition is: under a fixed pressure, the bonding time is 3 hours at a temperature of 120° C., the bonding time is 2 hours at a temperature of 140° C., or the bonding time is 50 minutes at a temperature of 160° C. After being heated and pressurized, the first conductive adhesive layer 514 is compressed to a thickness between 700 nm~5 um. At this time, a relatively tight fixation is formed between the piezoelectric layer 51 and the substrate 52 to complete an initial fabrication of the device.

Step 4: Post-Processing.

Thinning (grinding) the bonded device to reduce the thickness of the piezoelectric material layer 511, and then forming a fourth conductive layer 53 on the bonded device, such as "Ag" or "Cr+Au" as an upper electrode plate. Protective glue is continuously applied on the upper electrode plate. The device is soaked into a KOH solution. Since the protective glue can prevent corrosion of the KOH solution, the KOH solution further etches the substrate of the crystal-oriented silicon wafer until a required thickness of the substrate layer is obtained. At this time, the thickness of the substrate layer 521 is equivalent to the thickness of the first conductive adhesive layer 514. The device is taken out from the KOH solution, and the protective glue is removed using acetone or other more polar organic solvent. Finally, a slicing process is performed on the substrate 521 to finally obtain the energy converter.

In this embodiment, an epoxy resin is used as the first conductive adhesive layer. The epoxy resin is a viscous colloid at normal temperature. After being subjected to high temperature and high pressure for a certain period of time, it will be hardened and solidified, which achieves the stability of the connection between the piezoelectric material layer and the substrate. At the same time, the processing technology in this embodiment can be multiplexed with the integrated circuit technology, so that it can be compatible with the existing mainstream micro-nano device processing technology.

Embodiment 5

Figure 10:
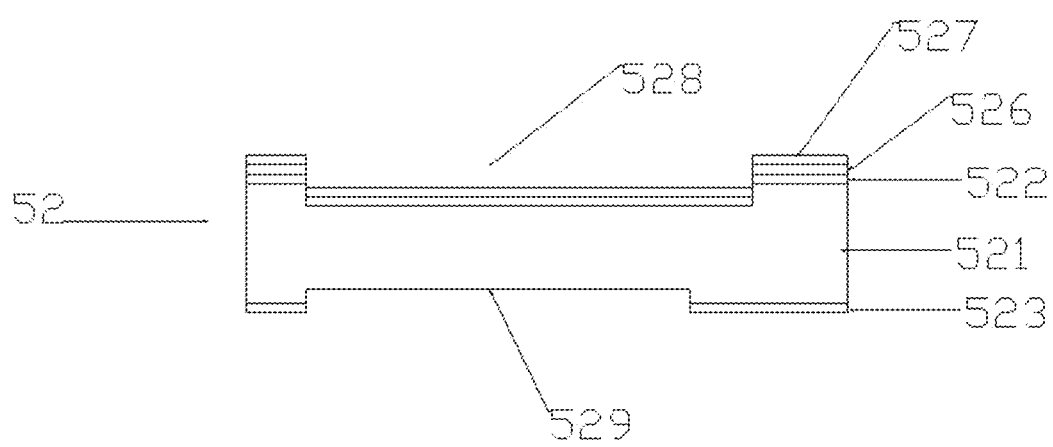
FIG. 10 is a structural diagram of a substrate layer in Embodiment 5 of the present invention.
Figure 11:
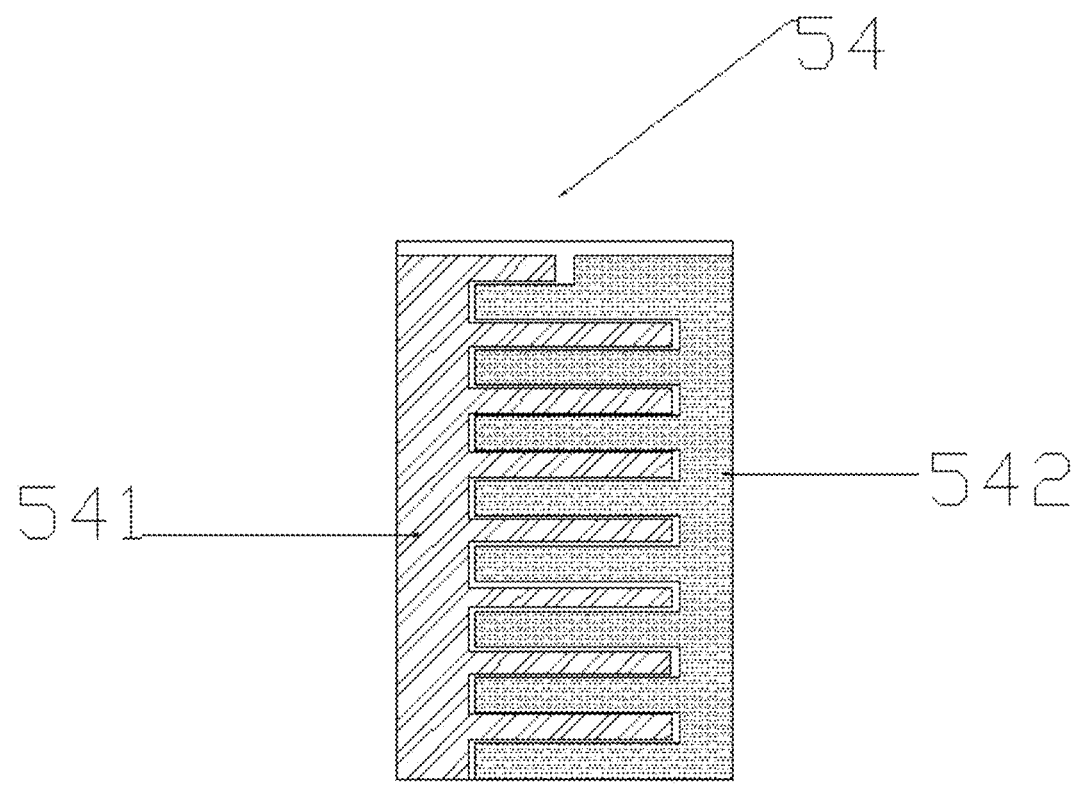
FIG. 11 is a structural diagram of an interdigital electrode in Embodiment 5 of the present invention.
Figure 12:
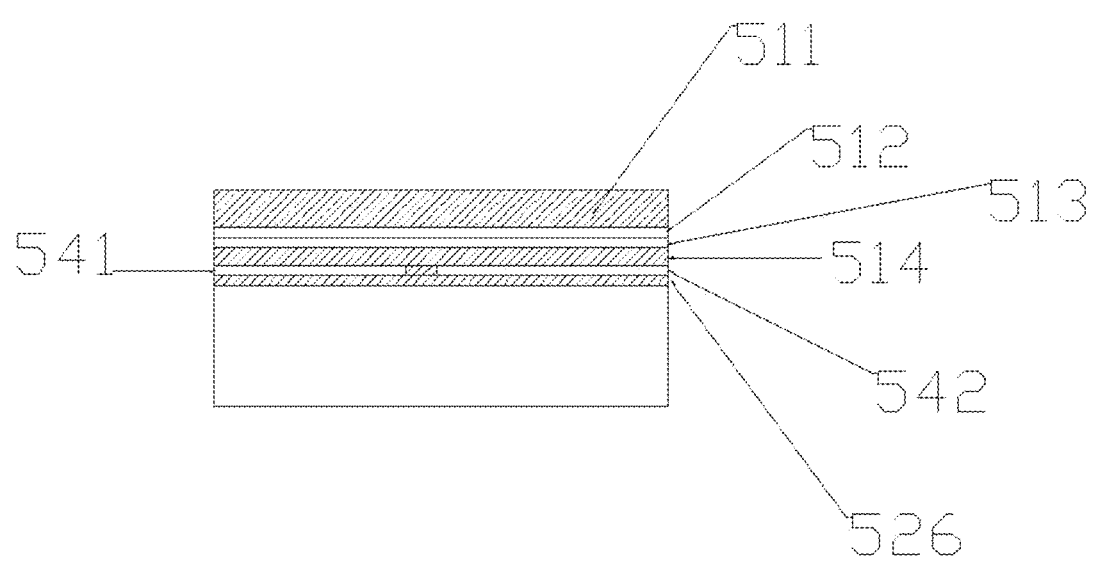
FIG. 12 is a structural diagram of an energy converter in Embodiment 5 of the present invention.

Please refer to FIGS. 10-12.

FIG. 10 is a structural diagram of a substrate layer in Embodiment 5 of the present invention.

FIG. 11 is a structural diagram of an interdigital electrode in Embodiment 5 of the present invention.

FIG. 12 is a structural diagram of an energy converter in Embodiment 5 of the present invention, and FIG. 12 is a structural diagram showing the structure from the top to the bottom with reference to FIG. 11.

On the basis of Embodiment 1, the energy converter may include a substrate 52. As shown in FIG. 10, the substrate 52 includes a substrate layer 521, a second conductive adhesive layer 526, a third conductive layer 527, and a piezoelectric layer 51. A first opening 55 and a second opening 56 are respectively disposed on a front surface and a back surface of the substrate layer 521. The second conductive adhesive layer 526 is located at the first opening 55. The third conductive layer 527 is located on the second conductive adhesive layer 526. The piezoelectric layer 51 is located on the third conductive layer 527, wherein a first surface of the piezoelectric layer 51 is flush with the first opening 55. The second opening 56 includes a raised end, and the raised end is a mass block. The substrate layer, the second conductive adhesive layer 526, the third conductive layer 527, and the piezoelectric layer 51 constitutes a cantilever beam, except the mass block.

As shown in FIG. 11, an interdigital electrode 54 is formed by the third conductive layer 527, which includes a first electrode layer 541 and a second electrode layer 542. The first electrode layer 541 and the second electrode 542 have opposite polarities.

The cantilever beam is used for fixedly connected with the electronically-controlled component housing 5. When the transmission unit is moving, the cantilever beam generates forced vibration under the driving action of environmental vibration, and the mass block located at the free end of the cantilever beam drives the cantilever beam to reciprocate up and down, thereby causing a zirconium titanate material layer on the cantilever beam to be stretched or compressed to produce mechanical strain. Then, the first electrode layer 541 and the second electrode layer 542 generate a current, that is, electrical energy is outputted outward.

As shown in FIG. 12, the piezoelectric layer 51 is provided with a piezoelectric material layer 511, a first seed layer 512, a first conductive layer 513, a first conductive adhesive layer 514 in the order from top to bottom, wherein the piezoelectric material layer 511 is a lead zirconate titanate material layer.

The specific processing technology of the energy converter is as follows:

Step 1: Preparation of the Piezoelectric Layer 51.

On the piezoelectric material layer 511, a Cr layer is sequentially sputtered as a first seed layer 512, an Au layer is evaporated as the first conductive layer 513, and finally an epoxy resin is applied as the first conductive adhesive layer 514. The Cr layer as the first seed layer 512 usually has a thickness of 200 Å to 2000 Å, but should not be lower than 200 Å. The Au layer as the first conductive layer 513 usually has a thickness of 2000 Å~10 nm, but should not be lower than 2000 Å. The first conducti adhesive layer 514 is an epoxy resin doped with silver crumb, which has bonding characteristics and electrical conductivity, and can perform good bonding.

Step 2: Pre-Treatment of the Substrate Layer 521.

A first protective layer 522 and a second protective layer 523 are respectively disposed on the front surface and the back surface of the substrate layer 521, a first recess 528 is formed between the first protective layer 522 and the substrate layer 521, and a second recess 529 is formed between the second protective layer 523 and the substrate layer 521, wherein the first protective layer 522 and the second protective layer 523 are $Si_3N_4$. The thickness of the $Si_3N_4$ layer is from 2000 Å to 5000 Å, but should not be less than 2000 Å. After etching the crystal silicon wafer with a 30% potassium hydroxide solution at a temperature of 70° C., the longitudinal height of the first recess 528 and the longitudinal height of the second recess 529 are increased. At this time, a second conductive adhesive layer 526 is disposed on the upper portion of the first protective layer 522 by means of whirl coating. The second conductive adhesive layer 526 is an epoxy conductive adhesive, and the second conductive adhesive layer 526 is cured. The curing process is: under a fixed pressure, the boding time is 1.8 hours at a temperature of 96° C., the bonding time is 1.2 hours at a temperature of 112° C., or the bonding time is 30 minutes at a temperature of 128° C., so that the epoxy conductive adhesive has a certain hardness and a certain plasticity. Then, the third conductive layer 527 is disposed on the second conductive adhesive layer 526 by evaporation, and the third conductive layer 527 is an Au layer. The Au layer is subjected to a small power scratch by a laser cutter machine, and then a fragile stress portion is formed on the surface of the Au layer. The substrate layer 521 is pre-treated to form a substrate.

Step 3: Bonding.

The piezoelectric layer 51 in Step 1 and the substrate 52 is Step 2 are bonded together under high temperature and high pressure. The lateral width of the piezoelectric layer 51 is smaller than the lateral width of the first recess 528. The bonding condition is: under a fixed pressure, a first bonding process is performed at a temperature of 96° C. for 1.8 hours, or at a temperature of 112° C. for 1.2 hours, or at a temperature of 128° C. for 30 minutes; and then a second bonding process is performed at a temperature of 90° C. for 2.1 hours, or at a temperature of 105° C. for 1.4 hours, or at a temperature of 120° C. for 35 minutes.

At this time, the first conductive adhesive layer 512 is the lowermost layer of the piezoelectric layer 51, the third conductive layer 527 is the uppermost layer of the substrate 52, and the lower layer of the third conductive layer 527 is the second conductive adhesive layer 526. The first conductive adhesive layer 514 and the second conductive adhesive layer 526 are both epoxy conductive adhesive layers, that is, the third conductive layer 527 is sandwiched between the two epoxy conductive adhesive layers. After the bonding condition of high temperature and high pressure, the third conductive layer 527 is appropriately stretched and breaks away from each other along the position of the laser scratch to form an interdigital electrode 54. The interdigital electrode 54 can achieve charge collection by using the structure of only one metal conductive layer to avoid waste.

Embodiment 6

Figure 13:
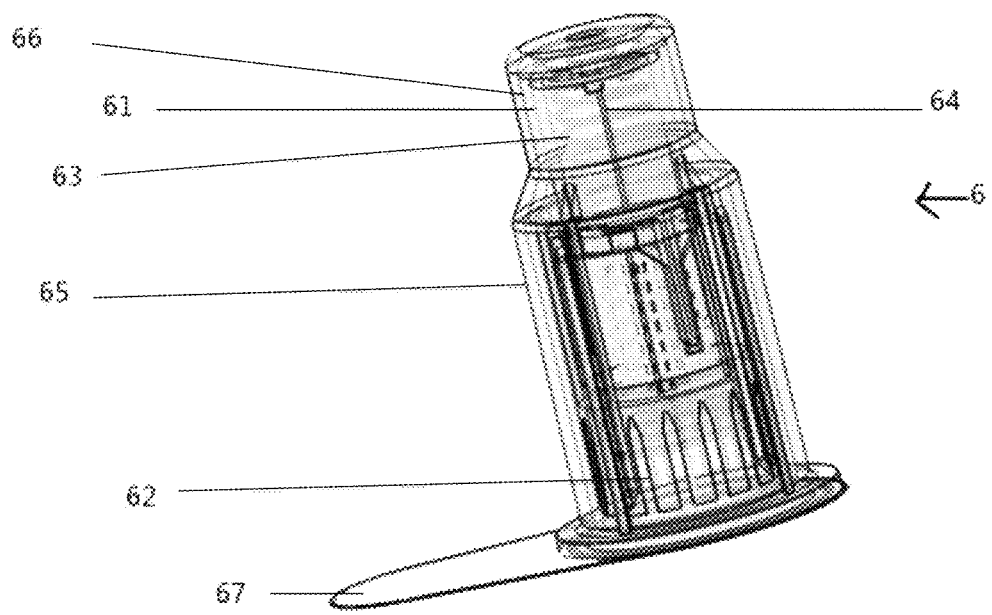
FIG. 13 is a structural diagram of an injection end of the safety syringe in Embodiment 6 of the present invention.

Please refer to FIG. 13.

FIG. 13 is a structural diagram of an injection end of the safety syringe in Embodiment 6 of the present invention.

The injection end 6 includes a protective casing 61, a needle base 62, a spring 63, an injection needle 64, a protective sleeve 65, a sliding sleeve 66, and a sealing strip 67. The injection needle 64 is fixed to the needle base 62. The spring 63 is fixed between the needle base 62 and the sliding sleeve 66, and fixing structures (not shown) are used to make the spring 63 fixed and not rotate. A first terminal of the spring 63 is connected to the needle base 62 and a second terminal of the spring 63 is connected to the sliding sleeve 66.

The protective sleeve 65 is fixedly connected with the needle base 62 to protect the protective casing 61 therein, so that the protective casing 61 is untouched when the injection end 6 is in an in-use status.

In a specific implementation of the present invention, the needle base 62 is further provided with a first sliding groove 621, a second sliding groove 622, and a limiting sheet 623. An outer surface of the sliding sleeve 66 is disposed with a positioning block 661 matched with the first sliding groove 621, the second sliding groove 622, and the limiting sheet 623 of the needle base 62. The number of the first sliding groove 621, the second sliding groove 622, and the limiting sheet 623 is the same of the number of the positioning block 661. For example, if the number of the first sliding groove 621, the second sliding groove, and the limiting sheet 623 is three, the number of the position block 661 is also three. The fixing structures for fixing the spring 63 can be disposed on the bar between the first sliding groove 621 and the second sliding groove 622 and the positioning block 661.

Figure 14:
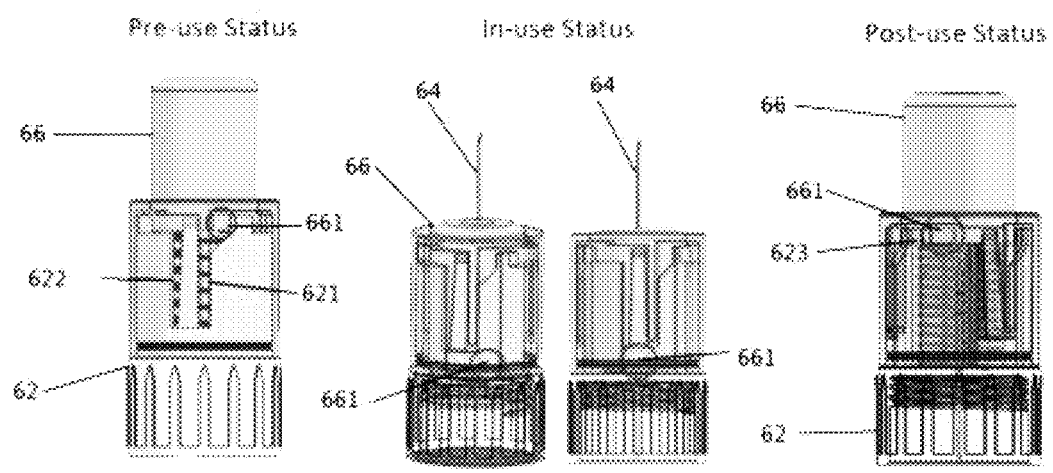
FIG. 14 is a schematic diagram showing different use statuses of an injection end of the safety syringe in Embodiment 6 of the present invention.

Please refer to FIG. 14.

FIG. 14 is a schematic diagram showing different use statuses of an injection end of the safety syringe in Embodiment 6 of the present invention.

Before assembling, the sliding sleeve 66 and the protective sleeve 65 needs to be rotated to the left or the right to cause a torsion force to the spring 63, and then the sliding sleeve 66 and the protective sleeve 65 are attached to the needle base 62. When the injection end 6 is in a pre-use status, the positioning block 661 of the sliding sleeve 66 is located at an opening of the first sliding groove 621 of the needle base 62. At this time, the tip of the injection needle 64 can be completely hidden inside the sliding sleeve 66, and the sliding sleeve 66 is subjected to a torsion force along a torsion direction of the spring 63.

When the injection end 6 is in an in-use status, the injection end 6 is pressed against skin, and the injection needle 64 is automatically exposed out from the sliding sleeve 66 and punctured. When the sliding sleeve 66 is pressed, the positioning block 661 of the sliding sleeve 66 moves downward along the first sliding groove 621 of the needle base 62. When the positioning block 661 reaches the bottom of the first sliding groove 621, the positioning block 661 moves to the left and enters the second sliding groove 622 by the torsion force of the spring 63.

When the injection end 6 is in a post-use status, the injection needle 64 is pulled out from the skin, then the sliding sleeve 66 moves upward due to an elastic force of the compressed spring 63, and the positioning block 661 of the sliding sleeve 66 moves upward along the second sliding groove 622. When the sliding sleeve 66 reaches the top, the sliding sleeve 66 moves to the left and locks by the torsion force of the spring 63. When the positioning block 661 reaches an opening of the second sliding groove 622, the limiting sheet 623 of the needle base 62 is bounced outward under the action of the positioning block 661. Finally, the sliding sleeve 66 is locked by the limiting sheet 623 to prevent the sliding sleeve 66 from being rotated to the initial state. At this time, the injection needle 64 is hidden inside the sliding sleeve 66 again.

The foregoing outlines features of several embodiments so that those skilled in the art may better understand the aspects of the present invention. Those skilled in the art should appreciate that they may readily use the present invention as a basis for designing or modifying other processes and structures for carrying out the same purposes and/or achieving the same advantages of the embodiments introduced herein. Those skilled in the art should also realize that such equivalent constructions do not depart from the spirit and scope of the present invention, and that they may make various changes, substitutions, and alterations herein without departing from the spirit and scope of the present invention.

What is claimed is:

1. An injection end for a safety syringe, the injection end comprising:
   a needle base;
   an injection needle, fixed to the needle base; and
   a needle guard assembly, connected to the needle base, the needle guard assembly comprising a protective casing and a spring, wherein a first terminal of the spring is connected to the needle base and a second terminal of the spring is connected to the protective casing;
   wherein when the injection end is in a pre-use status, the protective casing is rotated to the left or to the right to cause a torsion force to the spring, the injection needle is hidden inside the protective casing, and the protective casing is subjected to the torsion force along a torsion direction of the spring.

2. The injection end for a safety syringe in claim 1, wherein when the injection end is in an in-use status, the injection needle is pressed against skin, the injection needle is automatically exposed out from the protective casing and punctured, the spring is in a compressed state, and the protective casing is rotated out from a first locking groove on the protective casing by the torsion force of the spring.

3. The injection end for a safety syringe in claim 2, wherein when the injection end is in a post-use status, the injection needle is pulled out from the skin, the protective casing is moved away from the skin due to an elastic force of the compressed spring, the protective casing is automatically rotated due to the torsion force of the spring, and the injection needle is hidden inside the protective casing again.

4. The injection end for a safety syringe in claim 1, wherein the protective casing is further provided with a locking structure and a first limiting groove, and the locking structure further comprises a first locking groove and a second locking groove; and an outer surface of the needle base is disposed with a convex structure matched with the first limiting groove, the first locking groove, and the second locking groove.

5. The injection end for a safety syringe in claim 1, wherein the injection end further comprises a protective sleeve, and the protective sleeve is fixedly connected with the needle base to protect the protective casing therein, so that the protective casing is untouched when the injection end is in an in-use status, and the convex structure of the needle base is prevented from coming off the protective casing.

6. The injection end for a safety syringe in claim 1, wherein a bottom portion of the needle base is provided with a screw thread buckle, so that the injection end is detachably connected to a liquid storage device.

7. A safety syringe, comprising:
   an injection end, comprising:
     a needle base;
     an injection needle, fixed to the needle base; and
     a needle guard assembly, connected to the needle base, the needle guard assembly comprising a protective casing and a spring, wherein a first terminal of the spring is connected to the needle base and a second terminal of the spring is connected to the protective casing;
   a liquid storage device, comprising:
     a liquid storage container;
     a liquid storage sleeve, being sleeved on an outer surface of the liquid storage container, wherein the liquid storage container is detachably connected to the injection end; and
   a base, being detachably connected to the liquid storage device;
   wherein when the injection end is in a pre-use status, the protective casing is rotated to the left or to the right to cause a torsion force to the spring, the injection needle is hidden inside the protective casing, and the protective casing is subjected to the torsion force along a torsion direction of the spring.

8. The safety syringe in claim 7, wherein when the injection end is in an in-use status, the injection needle is pressed against skin, the injection needle is automatically exposed out from the protective casing and punctured, the spring is in a compressed state, and the protective casing is rotated out from a first locking groove on the protective casing by the torsion force of the spring.

9. The safety syringe in claim 8, wherein when the injection end is in a post-use status, the injection needle is pulled out from the skin, the protective casing is moved away from the skin due to an elastic force of the compressed spring, the protective casing is automatically rotated due to the torsion force of the spring, and the injection needle is hidden inside the protective casing again.

10. The safety syringe in claim 7, wherein the protective casing is further provided with a locking structure and a first limiting groove, and the locking structure further comprises a first locking groove and a second locking groove; and an outer surface of the needle base is disposed with a convex structure matched with the first limiting groove, the first locking groove, and the second locking groove.

11. The safety syringe in claim 7, wherein the injection end further comprises a protective sleeve, and the protective sleeve is fixedly connected with the needle base to protect the protective casing therein, so that the protective casing is untouched when the injection end is in an in-use status, and the convex structure of the needle base is prevented from coming off the protective casing.

12. The safety syringe in claim 7, wherein a bottom portion of the needle base is provided with a screw thread buckle, so that the injection end is detachably connected to the liquid storage device.

13. The safety syringe in claim 12, wherein the liquid storage container further comprises:
    a screw thread matched to the screw thread buckle, disposed on an upper portion of the liquid storage container, configured to achieve a detachable connection between the injection end and the liquid storage device; and
    a piston, disposed in a bottom portion of the liquid storage container, wherein the piston is slidablely moving inside the liquid storage container by an external force.

14. The safety syringe in claim 7, wherein the liquid storage sleeve further comprises:
    a visible window and a scale line, disposed on an outer surface of the liquid storage sleeve, allowing a user to observe a solvent dose inside the liquid storage container; and
    a clamping protrusion, disposed at a bottom portion of the liquid storage sleeve, configured to detachably connect with the base.

15. The safety syringe in claim 7, further comprising:
    a driving device, configured to drive the liquid storage container for injection, comprising:
    a power unit; and
    a transmission unit, electrically connected to the power unit;
    a microprocessor, configured to control the driving device;
    an energy storage component, configured to provide energy to the microprocessor and the driving device; and
    an energy converter, configured to convert mechanical energy into electrical energy, and transmit the electrical energy to the energy storage component;
    wherein the power unit, the energy storage component, the energy converter, and the microprocessor constitute an electronically-controlled component, mounted in an electronically-controlled component housing;
    wherein the electronically-controlled component housing is fixedly connected to the base.

16. The safety syringe in claim 15, wherein the energy converter further comprises:
    a substrate layer, wherein a first opening and a second opening are respectively disposed on a front surface and a back surface of the substrate layer;
    a second seed layer, located at the first opening;
    a second conductive layer, located on the second seed layer;
    a piezoelectric layer, located on the second conductive layer, wherein a first surface of the piezoelectric layer is flush with the first opening;
    a fourth conductive layer, located on the piezoelectric layer;
    wherein the second opening comprises a raised end, and the raised end is a mass block;
    wherein the substrate layer, the second feed layer, the second conductive layer, the piezoelectric layer, and the fourth conductive layer constitutes a cantilever beam, except the mass block.

17. The safety syringe in claim 15, wherein the energy converter comprises:
    a substrate layer, wherein a first opening and a second opening are respectively disposed on a front surface and a back surface of the substrate layer;
    a second conductive adhesive layer, located at the first opening;
    a third conductive layer, located on the second conductive adhesive layer;
    a piezoelectric layer, located on the third conductive layer, wherein a first surface of the piezoelectric layer is flush with the first opening;
    wherein the second opening comprises a raised end, and the raised end is a mass block;
    wherein the substrate layer, the second conductive adhesive layer, the third conductive layer, and the piezoelectric layer constitutes a cantilever beam, except the mass block.

18. The safety syringe in claim 17, wherein an interdigital electrode is formed by the third conductive layer, and the interdigital electrode further includes a first electrode layer and a second electrode layer, and the first electrode layer and the second electrode layer have opposite polarities.

* * * * *